US007251353B2

(12) United States Patent
Doi et al.

(10) Patent No.: US 7,251,353 B2
(45) Date of Patent: Jul. 31, 2007

(54) AUTOMATED METHOD OF PATIENT RECOGNITION USING CHEST RADIOGRAPHS

(75) Inventors: Kunio Doi, Chicago, IL (US); Junji Morishita, Chicago, IL (US); Shigehiko Katsuagawa, Chicago, IL (US)

(73) Assignee: University of Chicago, Chicago, IL (US)

( * ) Notice: Subject to any disclaimer, the term of this patent is extended or adjusted under 35 U.S.C. 154(b) by 677 days.

(21) Appl. No.: 10/358,337

(22) Filed: Feb. 5, 2003

(65) Prior Publication Data

US 2004/0101180 A1    May 27, 2004

Related U.S. Application Data

(60) Provisional application No. 60/428,939, filed on Nov. 26, 2002.

(51) Int. Cl.
*G06K 9/00* (2006.01)
(52) U.S. Cl. ................. 382/128; 382/218; 382/278
(58) Field of Classification Search ........ 382/128–134, 382/173, 199, 256, 266, 268, 218, 278; 600/374, 600/485, 508–514, 527, 528; 378/26
See application file for complete search history.

(56) References Cited

U.S. PATENT DOCUMENTS

| | | | | |
|---|---|---|---|---|
| 5,072,384 A | * | 12/1991 | Doi et al. ................... | 382/132 |
| 5,203,348 A | * | 4/1993 | Dahl et al. ................... | 607/129 |
| 5,431,161 A | * | 7/1995 | Ryals et al. ................. | 600/425 |
| 6,024,705 A | * | 2/2000 | Schlager et al. ............ | 600/508 |
| 6,335,980 B1 | * | 1/2002 | Armato et al. .............. | 382/132 |
| 6,459,925 B1 | * | 10/2002 | Nields et al. ............... | 600/427 |
| 6,836,558 B2 | * | 12/2004 | Doi et al. ................... | 382/131 |
| 6,901,280 B2 | * | 5/2005 | Pelletier et al. ............. | 600/410 |
| 6,912,301 B1 | * | 6/2005 | Lin et al. .................... | 382/128 |

* cited by examiner

*Primary Examiner*—Samir Ahmed
*Assistant Examiner*—Abolfazl Tabatabai
(74) *Attorney, Agent, or Firm*—Oblon, Spivak, McClelland, Maier & Neustadt, P.C.

(57) ABSTRACT

A method for determining whether a first medical image and a second medical image are medical images of the same patient, comprising selecting a first region in the first medical image; selecting a second region in the second medical image; determining a common region based on a boundary of the first region and a boundary of the second region; calculating a correlation coefficient based on image data from the first medical image in the common region and image data from the second medical image in the common region; and determining whether the first medical image and the second medical image are medical images of the same patient based on the correlation coefficient. Biological fingerprints from parts of chest radiographs such as thoracic fields, cardiac shadows, lung apices, superior mediastinum, and the right lower lung that includes the costophrenic angle, are used for the purpose of patient recognition and identification.

18 Claims, 11 Drawing Sheets

AUTOMATED METHOD OF PATIENT RECOGNITION USING CHEST RADIOGRAPHS

CROSS-REFERENCE TO RELATED APPLICATIONS

The present application is related to and claims priority to U.S. Provisional Application Ser. No. 60/428,939, filed Nov. 26, 2002. The contents of that application are incorporated herein by reference.

STATEMENT REGARDING FEDERALLY SPONSORED RESEARCH

The present invention was made in part with U.S. Government support under NIH Grant No. CA62625. The U.S. Government may have certain rights to this invention.

BACKGROUND OF THE INVENTION

Field of the Invention

The present invention relates generally to systems and methods for computer-aided patient recognition and identification using biological fingerprints obtained from radiographs.

The present invention also generally relates to computerized techniques for automated analysis of digital images, for example, as disclosed in one or more of U.S. Pat. Nos. 4,839,807; 4,841,555; 4,851,984; 4,875,165; 4,918,534; 5,072,384; 5,150,292; 5,224,177; 5,289,374; 5,319,549; 5,343,390; 5,359,513; 5,452,367; 5,463,548; 5,491,627; 5,537,485; 5,598,481; 5,622,171; 5,638,458; 5,657,362; 5,666,434; 5,673,332; 5,668,888; 5,732,697; 5,740,268; 5,790,690; 5,873,824; 5,881,124; 5,931,780; 5,974,165; 5,982,915; 5,984,870; 5,987,345; 6,011,862; 6,058,322; 6,067,373; 6,075,878; 6,078,680; 6,088,473; 6,112,112; 6,141,437; 6,185,320; 6,205,348; 6,240,201; 6,282,305; 6,282,307; 6,317,617; 6,335,980; 6,363,163; 6,442,287; 6,470,092; and 6,483,934; as well as U.S. patent application Ser. Nos. 08/173,935; 08/398,307 (PCT Publication WO 96/27846); 09/692,218; 09/759,333; 09/760,854; 09/773,636; 09/816,217; 09/830,562; 09/818,831; 09/860,574; 09/990,311; 09/990,310; 09/990,377; 10/270,674; 10/292,625; 60/331,995; and 60/395,305 and PCT patent applications PCT/US98/15165; PCT/US98/24933; PCT/US99/03287; PCT/US00/41299; PCT/US01/00680; PCT/US01/01478 and PCT/US01/01479, all of which are incorporated herein by reference.

The present invention includes the use of various technologies referenced and described in the above-noted U.S. Patents, as well as described in the references identified in the following LIST OF REFERENCES by the author(s) and year of publication and cross-referenced throughout the specification by reference to the respective number in parentheses, of the reference:

LIST OF REFERENCES

1. H. K. Huang, *PACS Basic principles and applications*, pp. 436-439, WILEY-LISS, New York, 1999.
2. A guideline to prevent medical accidents in radiology department, *Journal of Japan Radiological Society*, Vol.62, No.6, pp.63-88, 2002. (in Japanese)
3. Junji Morishita, Shigehiko Katsuragawa, Keisuke Kondo and Kunio Doi, An automated patient recognition method based on an image-matching technique using previous chest radiographs in the picture archiving and communication system environment, *Med. Phys.*, Vol.28 (6), pp1093-1097, 2001.
4. Asada N, Doi K, MacMahon H, Montner S M, Giger M L, Abe C, Wu Y, Potential usefulness of artificial neural network for differential diagnosis of interstitial lung diseases: A pilot study, *Radiology*, Vol.177, pp.857-860, 1990.

The entire contents of each related patent listed above and each reference listed in the LIST OF REFERENCES, are incorporated herein by reference.

DISCUSSION OF THE BACKGROUND

A large number of digital radiographs are routinely stored in the picture archiving and communication system (PACS) server in hospitals. For all of the images to be stored in the PACS server, it is important that images are stored in correct locations, e.g., in the proper patients' folders. If a patient's information associated with an acquired image does not match the correct information on the patient, a filing error will occur in the PACS environment. The main reasons for filing errors are related to human errors, such as incorrect input of patient information, accidental acquisition of radiographs of a wrong patient for a given examination, or occasionally imperfect design of the PACS [1][2]. Thus, the image may be assigned to a different patient name and may not be stored in the proper patient's folder. It is generally difficult to find such filing errors. Even if radiology personnel discover "wrong" images in the PACS server at a later date, it is difficult to re-file the image in the correct location in the PACS server. Filing errors may create serious problems, e.g., retrieval failure for a specific image from the PACS server [1], or radiologists may interpret incorrect images for a given patient. It is, therefore, desirable to discover wrong patients' images immediately after an acquired image is transferred to the PACS server.

Radiology personnel can usually identify radiological images in terms of patient information associated with the images such as the identification number, patient name, age, and gender. However, if the patient information associated with an image is not correct, the image may be identified as belonging to a different patient. The size and shape of the patients' physique, anatomic features, and specific abnormalities of the patients appearing in the radiological images also provide useful information for patient identification. However, if radiology personnel do not recognize a filing error, the "wrong" patient's image may be considered as the "correct" patient's image. Although such serious errors do not occur frequently in clinical situations, it is known that filing errors mainly caused by human mistakes occur in the PACS environment [1][2]. Therefore, an automated warning system would be useful.

It is well known that fingerprints, the retina, iris, face, and voice are commonly employed as biometrics for human identification for security purposes. Similarly, radiological images may be considered as "biological fingerprints" which may include useful image information for recognizing and identifying a patient.

The proper management of personal information has become increasingly important because of the significant progress made toward computerization and networking of information in recent years. It is known that biometrics such as fingerprints of a specific person do not change over time. On the other hand, the shape and size of the biological fingerprints in chest radiographs for a specific patient will change slightly due to positioning and/or pathologic changes in a patient. Although the biological fingerprints in chest radiographs will not have the same significance as the biometrics for human authentication, the biological fingerprints still have the advantages that they would not be stolen and may provide useful image information for recognizing and identifying a patient.

SUMMARY OF THE INVENTION

Accordingly, an object of this invention is to provide a method and system that discovers and prevents filing errors in archiving and retrieving images in the PACS environment.

These and other objects are achieved according to the invention by providing a method, system, and computer program product for determining whether a first medical image and a second medical image are medical images of a same patient, comprising: (1) selecting a first region in the first medical image; (2) selecting a second region in the second medical image; (3) determining a region common to the first region and the second region based on a boundary of the first region and a boundary of the second region; (4) calculating a correlation coefficient based on image data from the first medical image in the common region and image data from the second medical image in the common region; and (5) determining whether the first medical image and the second medical image are medical images of the same patient based on the correlation coefficient.

According to a second embodiment of the present invention, the steps of selecting the second region, determining the common region, and calculating the correlation coefficient, a predetermined number of times to obtain a plurality of correlation coefficients are repeated; and the largest correlation coefficient in the plurality of correlation coefficients is selected as the correlation coefficient.

According to an aspect of the present invention, the second region is selected within a search region of the second medical image, the search region based on the first region selected in the first medical image.

According to yet another aspect of the present invention, there is provided a method, system, and computer program product for determining whether a first medical image and a second medical image are medical images of a same patient, comprising: (1) selecting a plurality of first regions, each first region corresponding to one of a thoracic field, a cardiac shadow, a lung apex, a superior mediastinum, and a right lower lung in the first medical image; (2) selecting a respective plurality of second regions in the second medical image based on the plurality of first regions; (3) determining respective regions common to the plurality of first regions and the respective plurality of second regions; (4) calculating a set of correlation coefficients based on image data from the first medical image in each respective common region and image data from the second medical image in each respective common region; and (5) determining whether the first medical image and the second medical image are medical images of the same patient using an artificial neural network having the set of correlation coefficients as inputs.

A further aspect of the present invention is the use of thoracic fields, cardiac shadows, superior mediastinum, lung apices, a part of the right lung, and the right lower lung that includes the costophrenic angle as "biological fingerprints" in chest radiographs. Each biological fingerprint in a current chest radiograph is used as a template for determination of the correlation value with the corresponding biological fingerprint in a previous chest radiograph for patient recognition and identification.

The present invention provides an automated patient recognition method for digital chest radiographs based on a template-matching technique in which the correlation value between a current posteroanterior (PA) chest radiograph is compared with a previous radiograpgh. About 50% of wrong images can be identified correctly with the method of the present invention. This result is promising for recognizing and identifying a patient by using the image information on chest radiographs. Approximately 1.3% of filing errors were observed in a preliminary study of the method.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
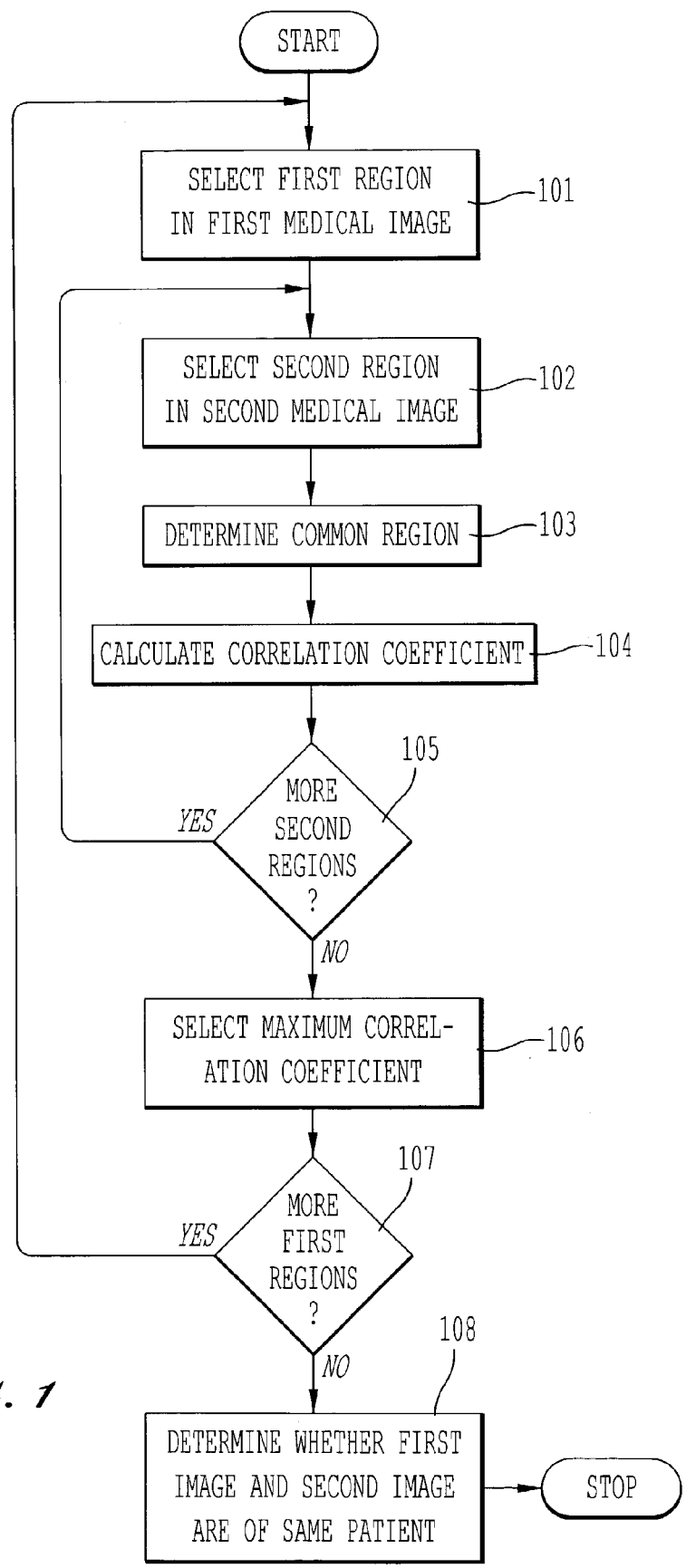
FIG. 1 is a flowchart of the method for determining whether a first medical image and a second medical image are medical images of a same patient according to the present invention.

Referring now to the drawings, wherein like reference numerals designate identical or corresponding parts throughout the several views, FIG. 1 is a flowchart of a method for determining whether a first medical image and a second medical image are medical images of the same patient. In step 101, a first region is selected in the first medical image. The first region corresponds, for example, to one of a thoracic field, a cardiac shadow, a lung apex, a superior mediastinum, and a right lower lung in the first medical image. In step 102, a second region is selected within a search region of the second medical image. The search region is based on the first region selected in the first medical image. In step 103, a region common to the first region and the second region is determined based on a boundary of the first region and a boundary of the second region. Next, in step 104, a correlation coefficient is calculated based on image data from the first medical image in the common region and image data from the second medical image in the common region. The calculation of the correlation is discusses in more detail below.

In step 105, an inquiry is made whether additional second images may be obtained within the search region of the second medical image. If so, steps 102-104 are then repeated a predetermined number of times. Each time a different second region is selected within the search region defined within the second medical image. If the answer to the inquiry in step 105 is no, step 106 is executed.

In step 106, the maximum correlation coefficient calculated in step 104 is selected as the correlation coefficient corresponding to the first region of step 101. In step 107, an inquiry is made whether additional first regions may be obtained within the first medical image. If so, steps 101-107 are repeated. Each time a different first region, e.g., a thoracic field, a cardiac shadow, a lung apex, or a superior mediastinum, is selected within the first medical image. If the answer to the inquiry in step 107 is no, step 108 is executed.

In step 108, it is determined whether the first medical image and the second medical image are medical images of the same patient based on the correlation coefficients associated with each first region. In one embodiment, an artificial neural network having the correlation coefficients selected in step 106 as inputs is used to determine whether the first and second medical images belong to the same patient. In another embodiment, a correlation coefficient is compared to a predetermined threshold to determine whether a first medical image and a second medical image are medical images of the same patient.

Figure 2:
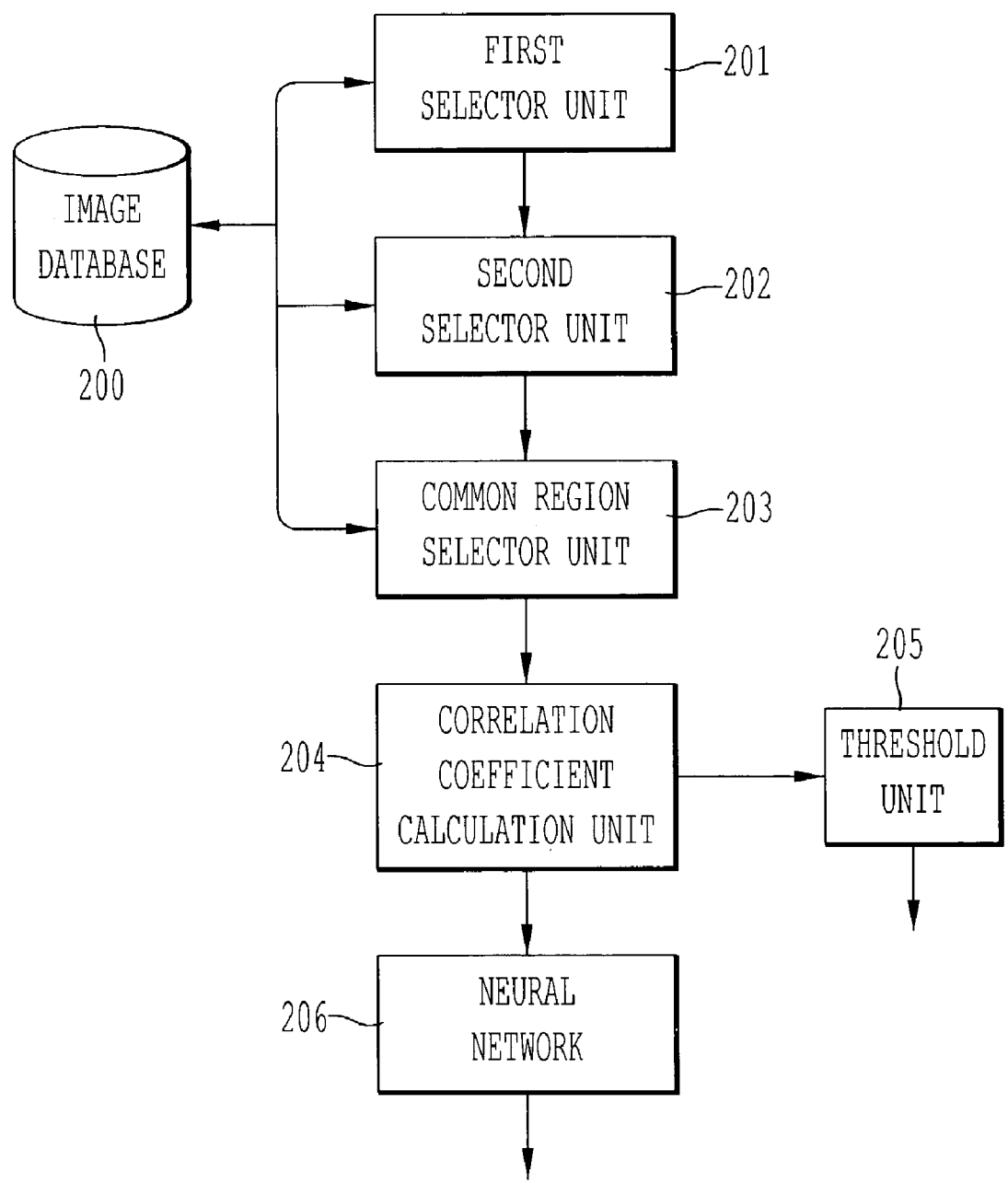
FIG. 2 is a block diagram of the system for determining whether a first medical image and a second medical image are medical images of a same patient according to the present invention.

The present invention may be better understood by reference to FIG. 2, which is a block diagram of the system for determining whether a first medical image and a second medical image are medical images of a same patient. The First Selector Unit 201 selects a first region in a first medical image stored in Image Database 200. Likewise, the Second Selector Unit 202 selects a second region in a second medical image. Next, Common Region Selector 203 determines the location of the region common to the first and second regions. Next, the Correlation Calculation Unit 204 calculates a correlation coefficient based on the common region of the first and second medical images. Next, based on the correlation coefficient, the Threshold Unit 205 determines whether the first and second medical images are of the same patient. Alternatively, the Neural Network 206 makes a similar determination based on at least one correlation coefficient computed by the Correlation Calculation Unit 204.

The method of the present invention was tested using a database consisting of 2000 PA chest radiographs that included 1000 current and 1000 previous images from 1000 patients. All images were obtained with a computed radiography system (CR, Fuji photo film, Tokyo, Japan) with a matrix size of 1760×1760 (0.2 mm pixel size) and ten-bit gray scale. The image matrix size was reduced to 64×64 by use of bilinear interpolation in order to reduce the computation time for subsequent processing [3].

Figure 3:
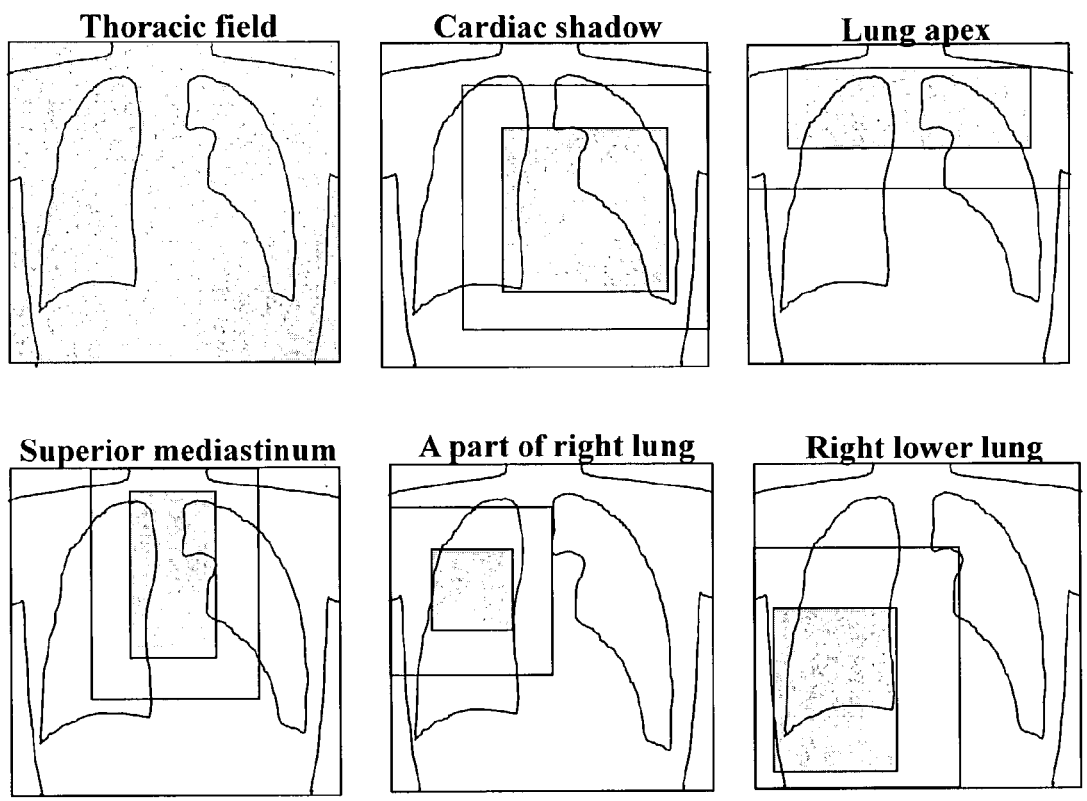
FIG. 3 illustrates the locations for six different biological fingerprints (gray rectangles) as templates, namely, thoracic fields, cardiac shadows, lung apices, superior mediastinum, a part of right lung, and right lower lung; the surrounding regions for each biological fingerprint indicate search areas used in a template matching technique.

Six different biological fingerprints in the chest radiographs, namely, the thoracic field, cardiac shadow, lung apex, superior mediastinum, a part of the right lung, and the right lower lung that includes the costophrenic angle, were used in this study. Each biological fingerprint in a chest radiograph includes distinctive anatomic structures. The locations and matrix sizes for the biological fingerprints are illustrated in FIG. 3 and Table 1. The template and search areas are illustrated in the images of FIG. 3 for simplicity. However, the template and the search areas were selected separately on the current and previous images, respectively.

Figure 4:
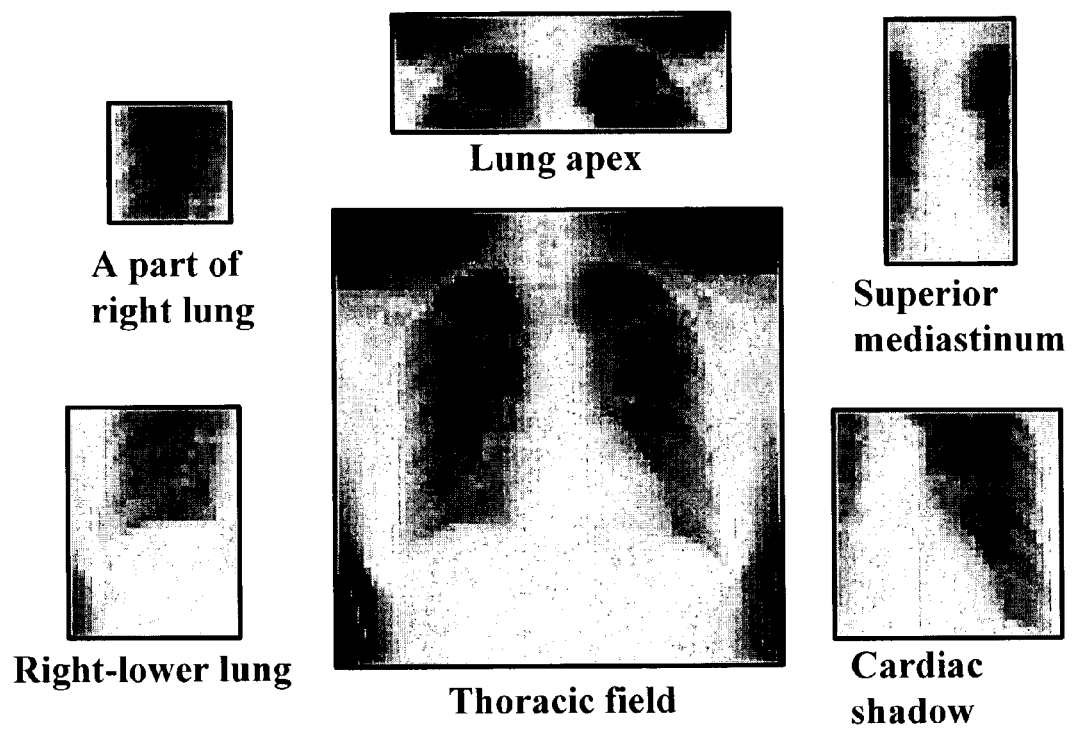
FIG. 4 shows various biological fingerprints extracted from a chest radiograph.

Images corresponding to six different biological fingerprints in a chest radiograph are shown in FIG. 4. The biological fingerprints on a current image were selected from fixed locations which were determined empirically, as templates for the subsequent template-matching technique. However, the biological fingerprints on the previous image were selected from locations where the templates on the current image were matched with the most similar regions by use of the template matching technique.

To examine the resemblance for each biological fingerprint between a current chest radiograph having image data A(i,j) and a previous chest radiograph having image data B(i,j), the correlation value C was determined (step 104) by the following equation:

$$C = \frac{1}{IJ} \sum_{j=1}^{J} \sum_{i=1}^{I} \frac{\{A(i,j) - \bar{a}\} \cdot \{B(i,j) - \bar{b}\}}{\sigma_A \cdot \sigma_B},$$

where $$\bar{a} = \frac{1}{IJ} \sum_{j=1}^{J} \sum_{i=1}^{I} A(i,j), \quad \bar{b} = \frac{1}{IJ} \sum_{j=1}^{J} \sum_{i=1}^{I} B(i,j)$$

$$\sigma_A = \sqrt{\frac{\sum_{j=1}^{J} \sum_{i=1}^{I} (A(i,j) - \bar{a})^2}{IJ}}, \quad \sigma_B = \sqrt{\frac{\sum_{j=1}^{J} \sum_{i=1}^{I} (B(i,j) - \bar{b})^2}{IJ}}$$

Here I and J indicate the matrix size of the area selected for the biological fingerprint. If the biological fingerprints in the two images are identical, C will be calculated as the maximum value of 1.0. A lower correlation value indicates less resemblance between the two biological fingerprints in the two images. Each biological fingerprint extracted from the current image was shifted horizontally and vertically in the search area for the biological fingerprint in the previous image for determination of the best match between the two images. The correlation value for each biological fingerprint with various image shifts was calculated only for the overlapped region of the two images. This method is useful for correcting for image variations due to different positioning in sequential chest radiographs [3].

Correlation values for biological fingerprints were determined for the current and previous images of the same "correct" 1000 patients, as were correlation values for 1000 combinations of current and previous images obtained with two different "wrong" patients. Then, histograms of correlation values for the same patients and also for the different patients were plotted for subsequent analysis. We set a threshold, e.g., 0.8, for correlation values to identify a patient. If the correlation value of the biological fingerprint between the current image and the previous image was larger than the threshold, then the current image was considered as belonging to the same, correct patient. On the other hand, if the correlation value of the biological fingerprint was smaller than the threshold, then the current image was identified as potentially belonging to a "wrong" patient. Thus, we can identify whether an unknown current image belongs to a "wrong" patient or a "correct" patient by histogram analysis.

The overall performance for each biological fingerprint was evaluated by use of receiver operating characteristic (ROC) curves. An ROC curve was generated for each biological fingerprint by changing the threshold of the correlation value in the histograms for the same patient and for different patients, such that the correlation value above or below the threshold is considered as indicating the same or different patients, respectively.

To improve the performance of the method further, artificial neural networks (ANNs) were applied to combine the results obtained from five of the biological fingerprints, excluding the part of the right lung. Three-layer, feed-forward ANNs with back-propagation algorithms [4] were employed in this study. The structure of ANNs included five input units, three hidden units, and one output unit. Input data for the ANNs were the correlation values obtained from thoracic fields, cardiac shadows, lung apices, superior mediastinum, and the right lower lung, whereas output values of 1.0 and 0 were used for the same and different patients, respectively, for training of the ANN. To estimate an average performance of the combined biological fingerprints, a jackknife test (or cross-validation) was used in which one-half of the database was selected randomly from the database as a training set for the ANNs, and the other half was used as a testing set for evaluation of the performance of the trained ANNs by ROC analysis. The jackknife test was repeated ten times for randomly selected different pairs of training and testing sets, and the average ROC curve and the corresponding $A_z$ value were obtained.

Figure 5A:
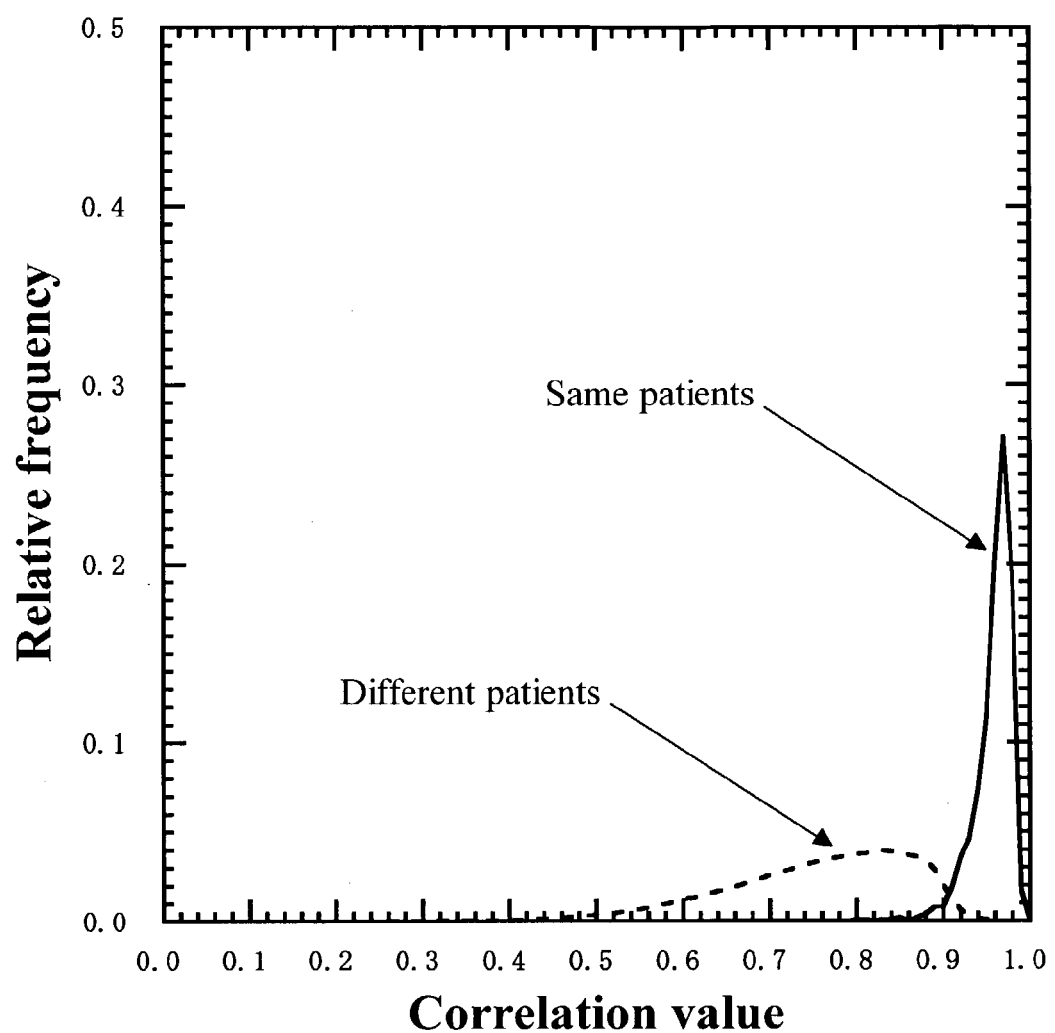
FIG. 5A is a histogram showing the correlation values between the current and previous images for the same patient (solid lines) and different patients (dashed lines) using the thoracic field as a biological fingerprint according to the present invention.
Figure 5B:
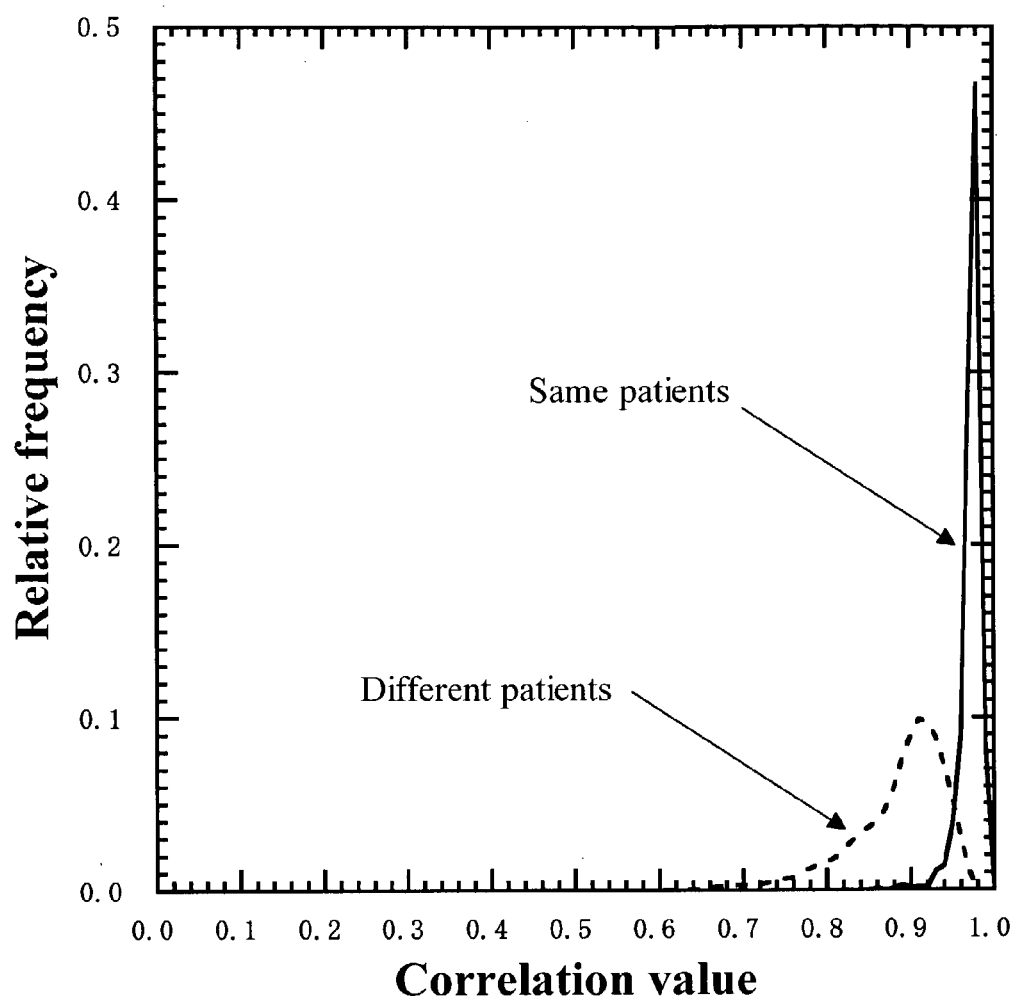
FIG. 5B is a histogram showing the correlation values between the current and previous images for the same patient (solid lines) and different patients (dashed lines) using the cardiac shadow as a biological fingerprint according to the present invention.
Figure 5C:
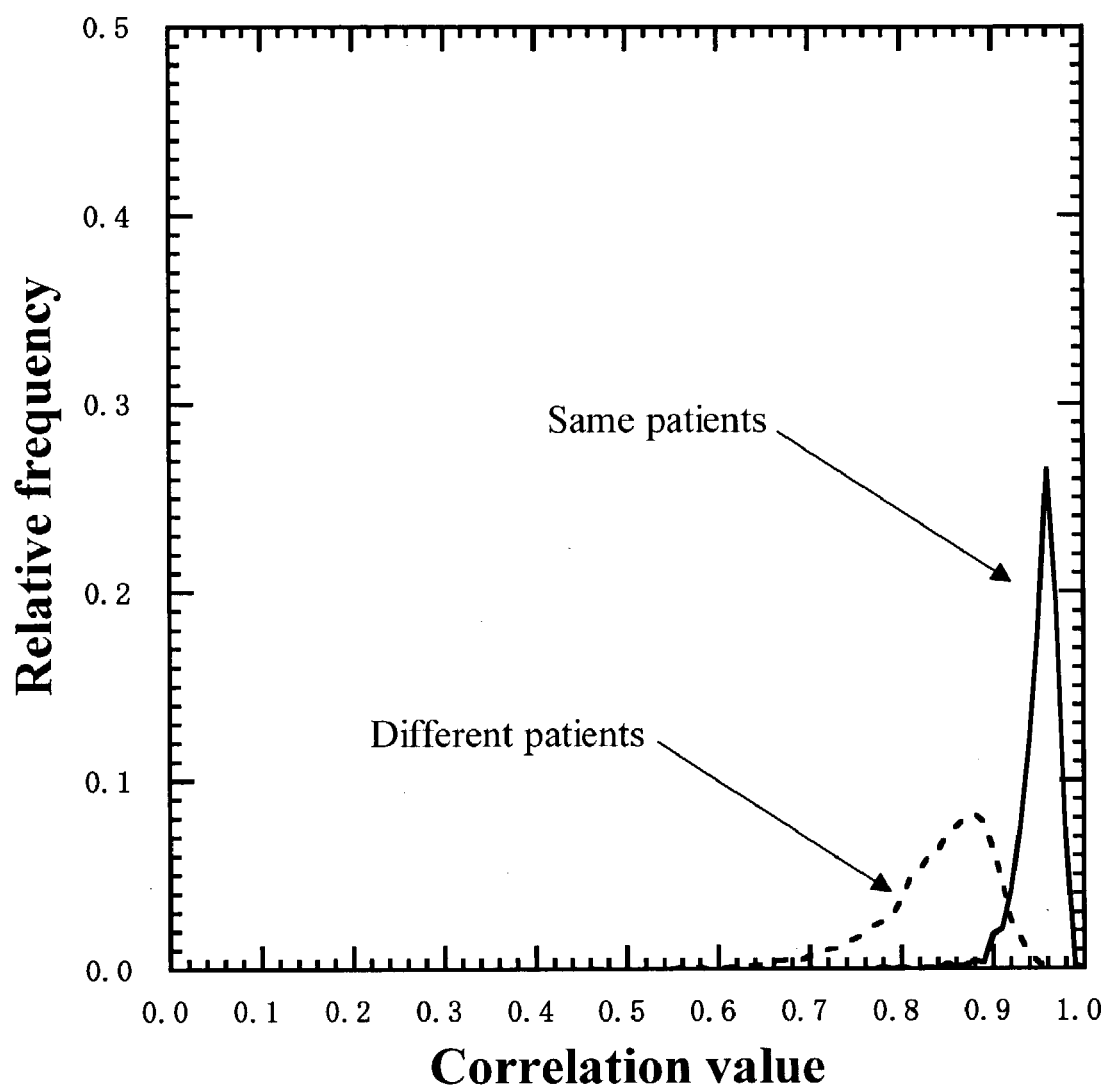
FIG. 5C is a histogram showing the correlation values between the current and previous images for the same patient (solid lines) and different patients (dashed lines) using the lung apices as a biological fingerprint according to the present invention.
Figure 5D:
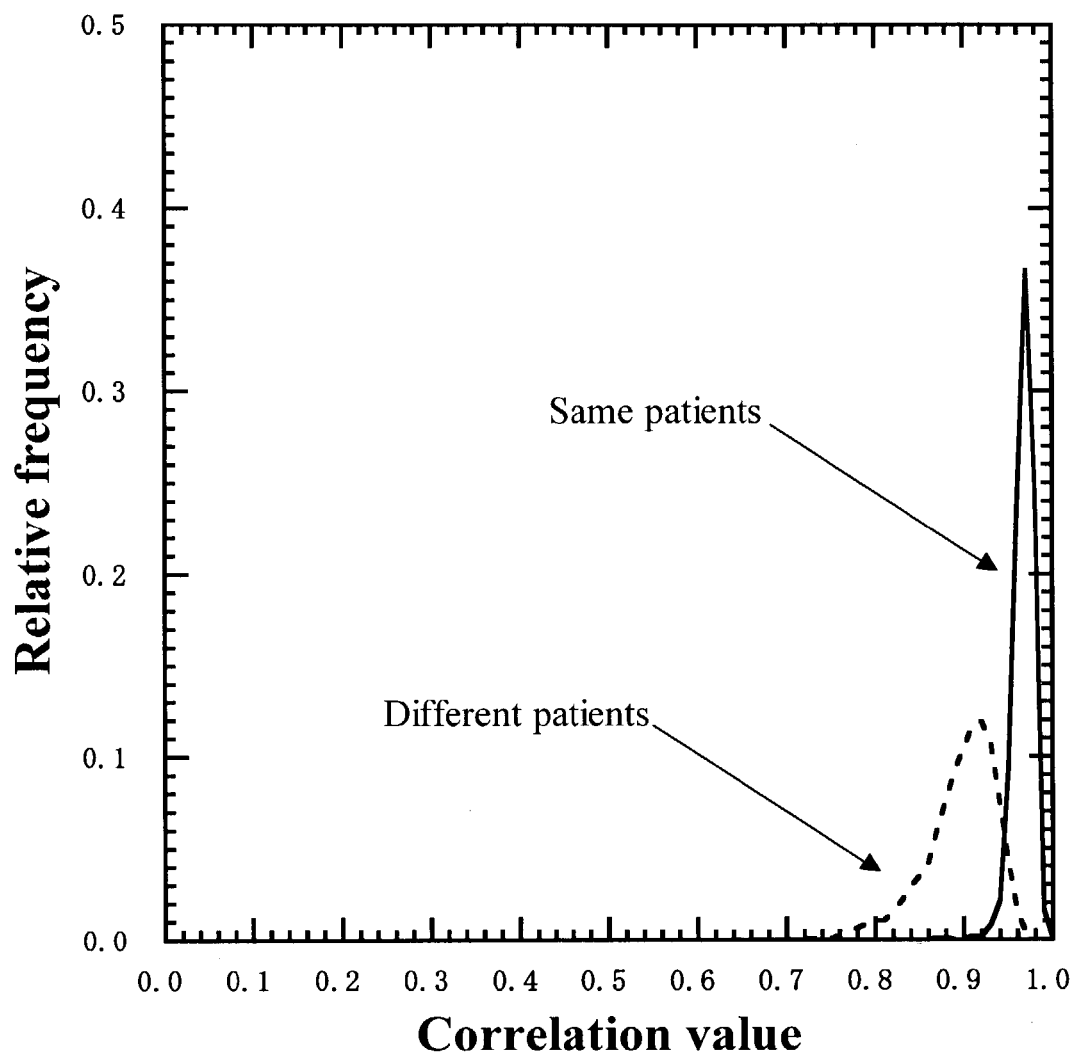
FIG. 5D is a histogram showing the correlation values between the current and previous images for the same patient (solid lines) and different patients (dashed lines) using the superior mediastinum as a biological fingerprint according to the present invention.
Figure 5E:
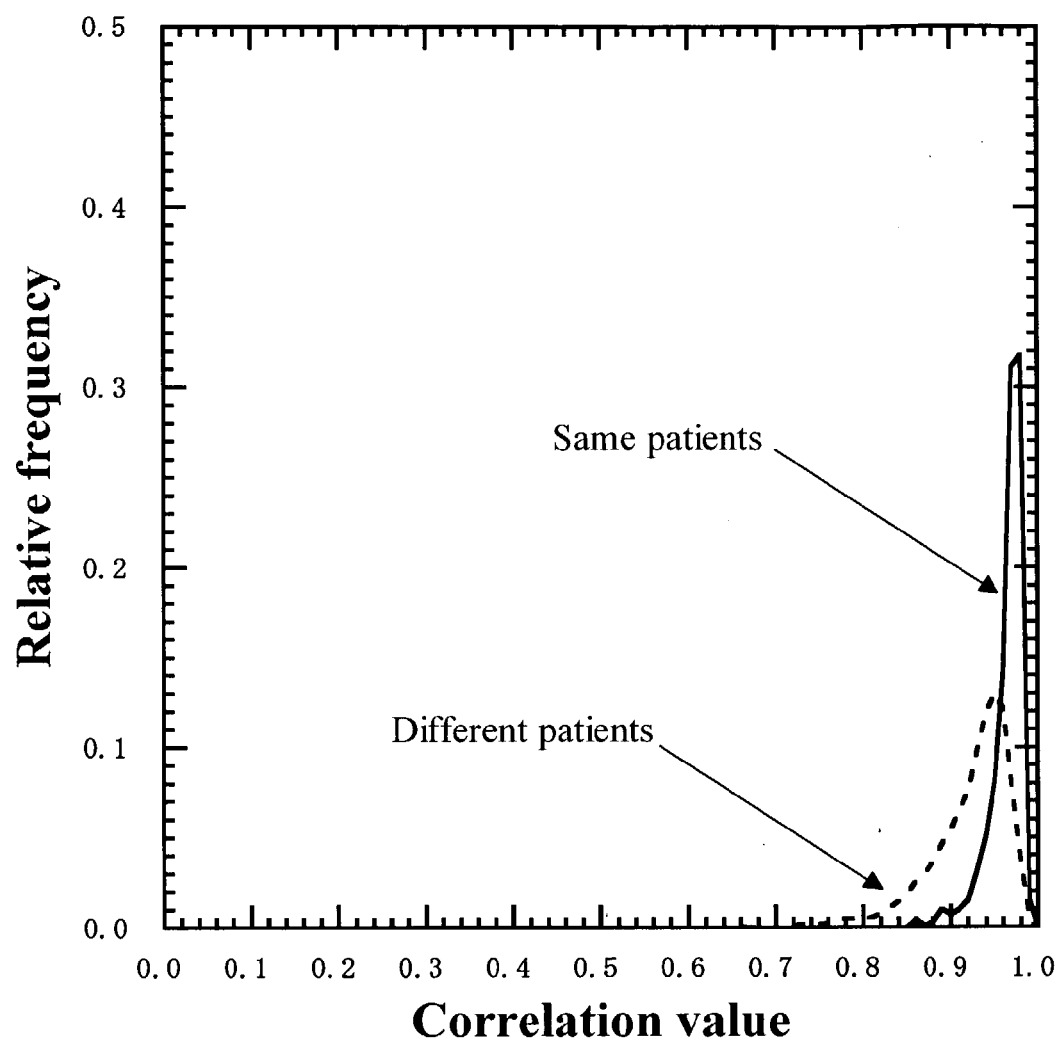
FIG. 5E is a histogram showing the correlation values between the current and previous images for the same patient (solid lines) and different patients (dashed lines) using a part of the right lung as a biological fingerprint according to the present invention.
Figure 5F:
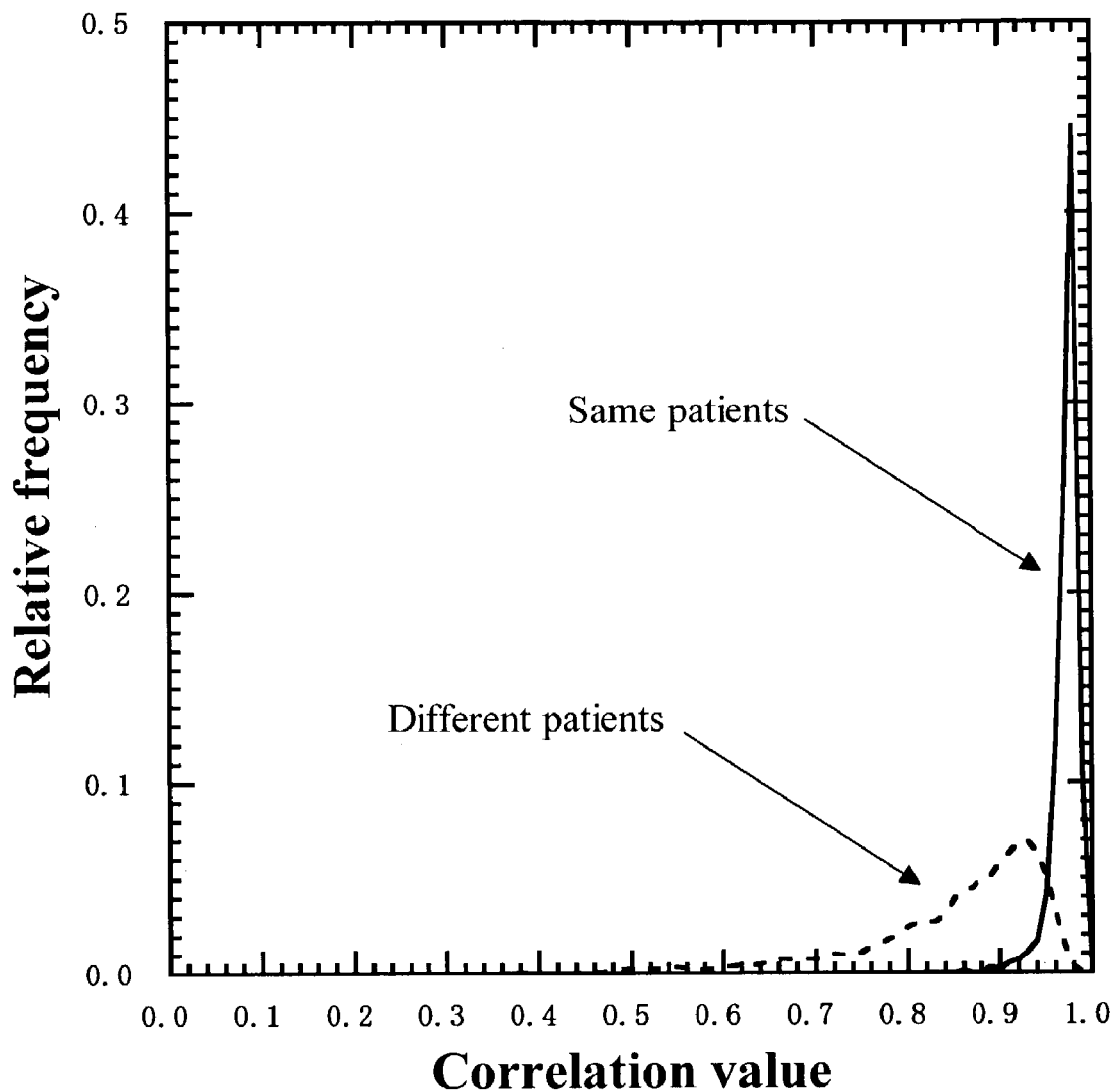
FIG. 5F is a histogram showing the correlation values between the current and previous images for the same patient (solid lines) and different patients (dashed lines) using the right lower lung as a biological fingerprint according to the present invention.

FIGS. 5A-5F show histograms of the correlation values obtained with six different biological fingerprints for the same patients and also for different patients. The correlation values between the current and previous images for the same, "correct" patients were generally greater than those for "wrong" patients in all of the biological fingerprints. It is important to note that most parts of the two histograms are separated in all of the biological fingerprints, although the two histograms on the part of the right lung in FIG. 5E are more overlapped compared with the histograms of the other biological fingerprints.

Figure 6:
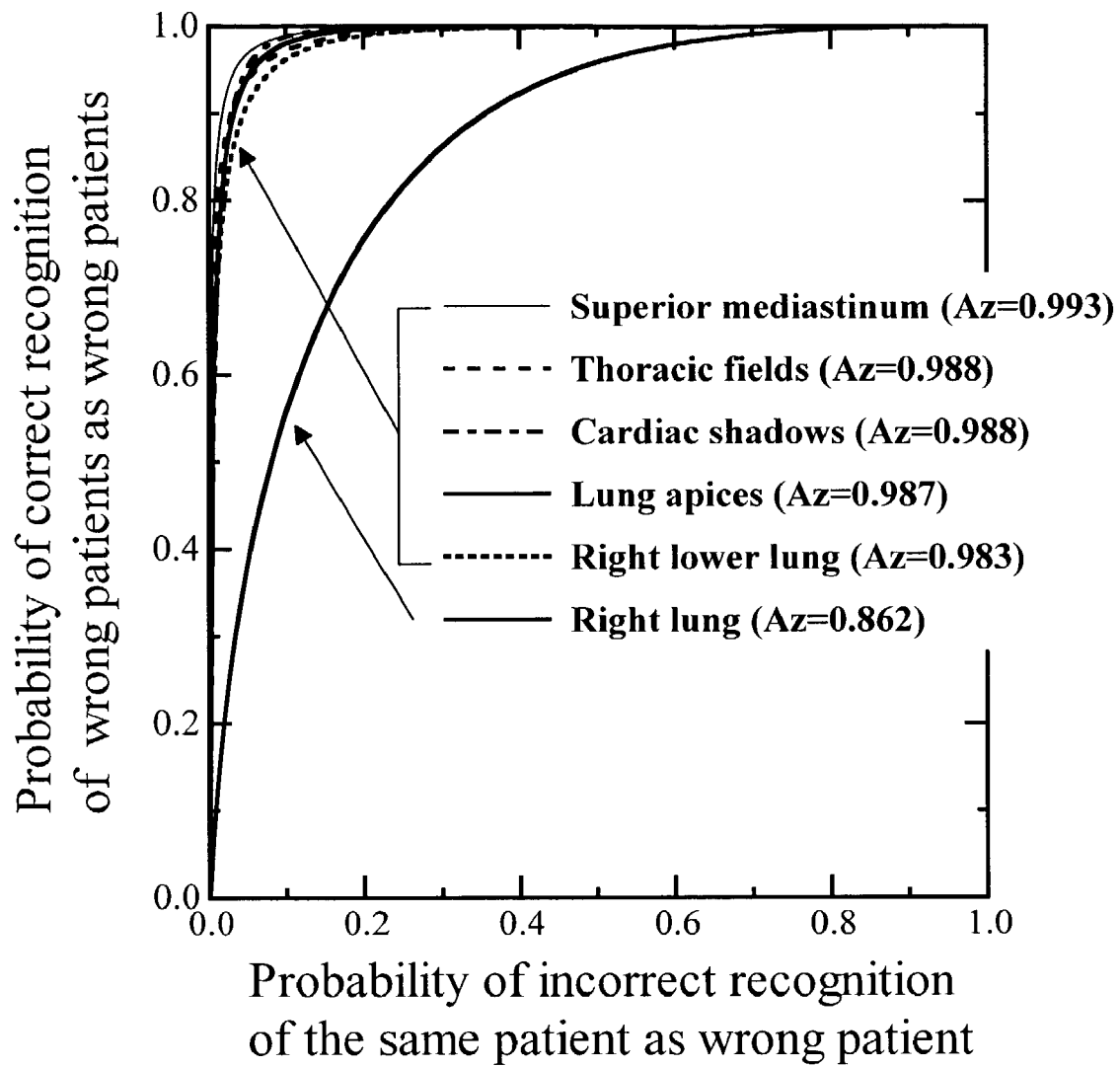
FIG. 6 illustrates the overall performance in terms of receiver operating characteristic (ROC) curves of the automated patient recognition method of the present invention using various biological fingerprints in chest radiographs.

The ROC curves in FIG. 6 indicate the overall performance of the automated patient recognition method by using the biological fingerprints in chest radiographs. The ROC curve shows the relationship between the probability of identifying different patients correctly as wrong patients and the probability of identifying the same patients incorrectly as wrong patients, which correspond to the fraction of true warnings and the fraction of false warnings, respectively, for the purpose of identifying wrong patients prior to storage in a wrong patient folder. ROC curves were located very close to the upper left corner except for a part of the right lung, abbreviated as right lung in the figure. The area under the ROC curve, $A_z$, for the superior mediastinum, thoracic fields, cardiac shadows, lung apices, and the right lower lung indicated considerably high values. This result clearly indicates that these five biological fingerprints have potential usefulness in identifying "wrong" patients. However, a part of the right lung may not be a useful biological fingerprint because of the smaller $A_z$ value than obtained for the others. The low performance with the right lung seems to be related to a general observation that the region in the middle lung does not usually include very strong and highly unique image features of individual patients.

The overall performance ($A_z$=0.996) obtained with the ANNs was improved compared to the results obtained with each of the biological fingerprints. These results indicate that each biological fingerprint includes slightly different features of the image, and that their combination can improve the overall performance. Finally, the probabilities of correct warning and wrong warning for different patients in the database were estimated for the same patient by using ANNs. A correct warning for different patients corresponds to the correct recognition of different patients as a wrong patient. On the other hand, a wrong warning for the same patient corresponds to the wrong recognition of the same patient as a wrong patient. The correct warning for different patients obtained with the combination of five biological fingerprints was estimated to be 84.6%, with 0.2% of the wrong warning for the same patient For the purposes of this description an image is defined to be a representation of a physical scene, in which the image has been generated by some imaging technology: examples of imaging technology could include television or CCD cameras or X-ray, sonar, or ultrasound imaging devices. The initial medium on which an image is recorded could be an electronic solid-state device, a photographic film, or some other device such as a photostimulable phosphor. That recorded image could then be converted into digital form by a combination of electronic (as in the case of a CCD signal) or mechanical/optical means (as in the case of digitizing a photographic film or digitizing the data from a photostimulable phosphor). The number of dimensions that an image could have could be one (e.g. acoustic signals), two (e.g. X-ray radiological images), or more (e.g. nuclear magnetic resonance images).

As disclosed in cross-referenced pending patent application Ser. No. 09/773,636, FIG. 9 of that patent application is a schematic illustration of a general purpose computer 900 which can be programmed according to the teachings of the present invention. In FIG. 9 of the cross-referenced application Ser. No. 09/773,636, the computer 900 can be used to implement the processes of the present invention, wherein the computer includes, for example, a display device 902 (e.g., a touch screen monitor with a touch-screen interface, etc.), a keyboard 904, a pointing device 906, a mouse pad or digitizing pad 908, a hard disk 910, or other fixed, high density media drives, connected using an appropriate device bus (e.g., a SCSI bus, an Enhanced IDE bus, an Ultra DMA bus, a PCI bus, etc.), a floppy drive 912, a tape or CD ROM drive 914 with tape or CD media 916, or other removable media devices, such as magneto-optical media, etc., and a mother board 918. The mother board 918 includes, for example, a processor 920, a RAM 922, and a ROM 924

(e.g., DRAM, ROM, EPROM, EEPROM, SRAM, SDRAM, and Flash RAM, etc.), I/O ports 926 which may be used to couple to an image acquisition device and optional special purpose logic devices (e.g., ASICs, etc.) or configurable logic devices (e.g., GAL and re-programmable FPGA) 928 for performing specialized hardware/software functions, such as sound processing, image processing, signal processing, neural network processing, automated classification, etc., a microphone 930, and a speaker or speakers 932.

As stated above, the system of the present invention includes at least one computer readable medium. Examples of computer readable media are compact discs, hard disks, floppy disks, tape, magneto-optical disks, PROMs (EPROM, EEPROM, Flash EPROM), DRAM, SRAM, SDRAM, etc. Stored on any one or on a combination of computer readable media, the present invention includes software for controlling both the hardware of the computer and for enabling the computer to interact with a human user. Such software may include, but is not limited to, device drivers, operating systems and user applications, such as development tools. Such computer readable media further includes the computer program product of the present invention for performing any of the processes according to the present invention, described above. The computer code devices of the present invention can be any interpreted or executable code mechanism, including but not limited to scripts, interpreters, dynamic link libraries, Java classes, and complete executable programs, etc.

The programming of general purpose computer 900 (disclosed in cross-referenced pending patent application Ser. No. 09/773,636) may include a software module for digitizing and storing images obtained from film or an image acquisition device. Alternatively, the present invention can also be implemented to process digital data derived from images obtained by other means, such as a picture archive communication system (PACS). In other words, the digital images being processed may be in existence in digital form and need not be converted to digital form in practicing the invention.

Accordingly, the mechanisms and processes set forth in the present description may be implemented using a conventional general purpose microprocessor or computer programmed according to the teachings in the present specification, as will be appreciated by those skilled in the relevant art(s). Appropriate software coding can readily be prepared by skilled programmers based on the teachings of the present disclosure, as will also be apparent to those skilled in the relevant art(s). However, as will be readily apparent to those skilled in the art, the present invention also may be implemented by the preparation of application-specific integrated circuits or by interconnecting an appropriate network of conventional component circuits. The present invention thus also includes a computer-based product which may be hosted on a storage medium and include instructions which can be used to program a general purpose microprocessor or computer to perform processes in accordance with the present invention. This storage medium can include, but is not limited to, any type of disk including floppy disks, optical disks, CD-ROMs, magneto-optical disks, ROMs, RAMs, EPROMs, EEPROMs, flash memory, magnetic or optical cards, or any type of media suitable for storing electronic instructions.

Obviously, numerous modifications and variations of the present invention are possible in light of the above teachings. The method of recognizing biological fingerprints according to the present invention can be applied to medical images other than radiological images of the lung. Moreover, biological fingerprints would be useful features not only for patient recognition and identification, but also in searching the same patient's images or similar images from the PACS server. It is therefore to be understood that within the scope of the appended claims, the invention may be practiced otherwise than as specifically described herein.

TABLE 1

| Biological fingerprints | for template | | for search area | |
|---|---|---|---|---|
| | matrix size | location | matrix size | location |
| Thoracic field | 64 × 64 | (1, 1) | 64 × 64 | (1, 1) |
| Cardiac shadow | 32 × 32 | (25, 17) | 48 × 48 | (17, 9) |
| Lung apex | 48 × 16 | (9, 5) | 64 × 28 | (1, 1) |
| Superior mediastinum | 16 × 32 | (25, 5) | 32 × 44 | (17, 1) |
| A part of right lung | 16 × 16 | (9, 17) | 32 × 32 | (1, 9) |
| Right lower lung | 24 × 32 | (5, 29) | 40 × 48 | (1, 17) |

The matrix size and location (coordinates for top left and bottom right) for various biological fingerprints as templates, and for the search area for template matching. The biological fingerprints and the search area were selected in current and previous chest radiographs with a matrix size of 64 × 64.

The invention claimed is:

1. A method for determining whether a first medical image and a second medical image are medical images of a same patient, comprising:
    selecting a first region in the first medical image;
    selecting a second region in the second medical image;
    determining a region common to the first region and the second region based on a boundary of the first region and a boundary of the second region;
    calculating a correlation coefficient based on image data from the first medical image in the common region and image data from the second medical image in the common region; and
    determining whether the first medical image and the second medical image are medical images of the same patient based on the correlation coefficient.

2. The method of claim 1, wherein the step of determining whether the first medical image and the second medical image are medical images of the same patient comprises:
    determining whether the correlation coefficient exceeds a predetermined threshold.

3. The method of claim 1, wherein the step of selecting a second region comprises:
    selecting the second region within a search region of the second medical image, the search region based on the first region selected in the first medical image.

4. The method of claim 3, further comprising:
    repeating the steps of selecting the second region, determining the common region, and calculating the correlation coefficient, a predetermined number of times to obtain a plurality of correlation coefficients; and
    selecting a largest correlation coefficient in the plurality of correlation coefficients as the correlation coefficient.

5. The method of claim 1, wherein the calculating step comprises:
    calculating the correlation coefficient (C) as:

$$C = \frac{1}{IJ} \sum_{j=1}^{J} \sum_{i=1}^{I} \frac{\{A(i,j) - \bar{a}\} \cdot \{B(i,j) - \bar{b}\}}{\sigma_A \cdot \sigma_B}$$

-continued $$\bar{a} = \frac{1}{IJ}\sum_{j=1}^{J}\sum_{i=1}^{I} A(i,j), \quad \bar{b} = \frac{1}{IJ}\sum_{j=1}^{J}\sum_{i=1}^{I} B(i,j)$$

$$\sigma_A = \sqrt{\frac{\sum_{j=1}^{J}\sum_{i=1}^{I}(A(i,j)-\bar{a})^2}{IJ}}, \quad \sigma_B = \sqrt{\frac{\sum_{j=1}^{J}\sum_{i=1}^{I}(B(i,j)-\bar{b})^2}{IJ}}$$

wherein A(i,j) is the image data from the first medical image, B(i,j) is the image data from the second medical image, and I and J indicate a size of the common area.

6. A method for determining whether a first medical image and a second medical image are medical images of a same patient, comprising:
   selecting a plurality of first regions, each first region corresponding to one of a thoracic field, a cardiac shadow, lung apex, a superior mediastinum, and a right lower lung in the first medical image;
   selecting a respective plurality of second regions in the second medical image based on the plurality of first regions;
   determining respective regions common to the plurality of first regions and the respective plurality of second regions;
   calculating a set of correlation coefficients based on image data from the first medical image in each respective common region and image data from the second medical image in each respective common region; and
   determining whether the first medical image and the second medical image are medical images of the same patient using an artificial neural network having the set of correlation coefficients as inputs.

7. A computer program embodied in a computer readable medium, the computer program comprising:
   instructions for selecting a first region in the first medical image;
   instructions for selecting a second region in the second medical image;
   instructions for determining a region common to the first region and the second region based on a boundary of the first region and a boundary of the second region;
   instructions for calculating a correlation coefficient based on image data from the first medical image in the common region and image data from the second medical image in the common region; and
   instructions for determining whether the first medical image and the second medical image are medical images of the same patient based on the correlation coefficient.

8. The computer program of claim 7, wherein the instructions for determining whether the first medical image and the second medical image are medical images of the same patient comprise:
   instructions for determining whether the correlation coefficient exceeds a predetermined threshold.

9. The computer program of claim 7, wherein the instructions for selecting a second region comprise:
   instructions for selecting the second region within a search region of the second medical image, the search region based on the first region selected in the first medical image.

10. The computer program of claim 9, further comprising:
    instructions for repeating the instructions for selecting the second region, determining the common region, and calculating the correlation coefficient, a predetermined number of times to obtain a plurality of correlation coefficients; and
    instructions for selecting a largest correlation coefficient in the plurality of correlation coefficients as the correlation coefficient.

11. The computer program of claim 7, wherein the instructions for calculating comprise:
    instructions for calculating the correlation coefficient (C) as:

$$C = \frac{1}{IJ}\sum_{j=1}^{J}\sum_{i=1}^{I} \frac{\{A(i,j)-\bar{a}\}\cdot\{B(i,j)-\bar{b}\}}{\sigma_A \cdot \sigma_B}$$

$$\bar{a} = \frac{1}{IJ}\sum_{j=1}^{J}\sum_{i=1}^{I} A(i,j), \quad \bar{b} = \frac{1}{IJ}\sum_{j=1}^{J}\sum_{i=1}^{I} B(i,j)$$

$$\sigma_A = \sqrt{\frac{\sum_{j=1}^{J}\sum_{i=1}^{I}(A(i,j)-\bar{a})^2}{IJ}}, \quad \sigma_B = \sqrt{\frac{\sum_{j=1}^{J}\sum_{i=1}^{I}(B(i,j)-\bar{b})^2}{IJ}}$$

wherein A(i,j) is the image data from the first medical image, B(i,j) is the image data from the second medical image, and I and J indicate a size of the common area.

12. A computer program embodied in a computer readable medium, the computer program configured to determine whether a first medical image and a second medical image are medical images of a same patient, comprising:
    instructions for selecting a plurality of first regions, each first region corresponding to one of a thoracic field, a cardiac shadow, lung apex, a superior mediastinum, and a right lower lung in the first medical image;
    instructions for selecting a respective plurality of second regions in the second medical image based on the plurality of first regions;
    instructions for determining respective regions common to the plurality of first regions and the respective plurality of second regions;
    instructions for calculating a set of correlation coefficients based on image data from the first medical image in each respective common region and image data from the second medical image in each respective common region; and
    instructions for determining whether the first medical image and the second medical image are medical images of the same patient using an artificial neural network having the set of correlation coefficients as inputs.

13. A system for determining whether the first medical image and the second medical image are medical images of the same patient, comprising:
    means for selecting a first region in the first medical image;
    means for selecting a second region in the second medical image;
    means for determining a region common to the first region and the second region based on a boundary of the first region and a boundary of the second region;
    means for calculating a correlation coefficient based on image data from the first medical image in the common region and image data from the second medical image in the common region; and means for determining whether the first medical image and the second medical image are medical images of the same patient based on the correlation coefficient.

14. The system of claim 13, wherein the means for determining whether the first medical image and the second medical image are medical images of the same patient comprise:

means for determining whether the correlation coefficient exceeds a predetermined threshold.

15. The system of claim 13, wherein the means for selecting a second region comprises:

means for selecting the second region within a search region of the second medical image, the search region based on the first region selected in the first medical image.

16. The system of claim 15, further comprising:

means for causing the repeated execution of the means for selecting the second region, means for determining the common region, and means for calculating the correlation coefficient, a predetermined number of times to obtain a plurality of correlation coefficients; and means for selecting a largest correlation coefficient in the plurality of correlation coefficients as the correlation coefficient.

17. The system of claim 13, wherein the means for calculating comprises:

means for calculating the correlation coefficient (C) as:

$$C = \frac{1}{IJ} \sum_{j=1}^{J} \sum_{i=1}^{I} \frac{\{A(i,j) - \bar{a}\} \cdot \{B(i,j) - \bar{b}\}}{\sigma_A \cdot \sigma_B}$$

$$\bar{a} = \frac{1}{IJ} \sum_{j=1}^{J} \sum_{i=1}^{I} A(i,j), \quad \bar{b} = \frac{1}{IJ} \sum_{j=1}^{J} \sum_{i=1}^{I} B(i,j)$$

-continued $$\sigma_A = \sqrt{\frac{\sum_{j=1}^{J} \sum_{i=1}^{I} (A(i,j) - \bar{a})^2}{IJ}}, \quad \sigma_B = \sqrt{\frac{\sum_{j=1}^{J} \sum_{i=1}^{I} (B(i,j) - \bar{b})^2}{IJ}}$$

wherein A(i,j) is the image data from the first medical image, B(i,j) is the image data from the second medical image, and I and J indicate a size of the common area.

18. A system for determining whether a first medical image and a second medical image are medical images of a same patient, comprising:

means for selecting a plurality of first regions, each first region corresponding to one of a thoracic field, a cardiac shadow, lung apex, a superior mediastinum, and a right lower lung in the first medical image;

means for selecting a respective plurality of second regions in the second medical image based on the plurality of first regions;

means for determining respective regions common to the plurality of first regions and the respective plurality of second regions;

means for calculating a set of correlation coefficients based on image data from the first medical image in each respective common region and image data from the second medical image in each respective common region; and means for determining whether the first medical image and the second medical image are medical images of the same patient using an artificial neural network having the set of correlation coefficients as inputs.

\* \* \* \* \*

UNITED STATES PATENT AND TRADEMARK OFFICE
CERTIFICATE OF CORRECTION

PATENT NO. : 7,251,353 B2  Page 1 of 1
APPLICATION NO. : 10/358337
DATED : July 31, 2007
INVENTOR(S) : Doi et al.

It is certified that error appears in the above-identified patent and that said Letters Patent is hereby corrected as shown below:

On the title page, Item (75), the Inventors information is incorrect. Item (75) should read:

-- (75) Inventors: Kunio Doi, Chicago, IL (US); Junji Morishita, Sonobe (JP); Shigehiko Katsuagawa, Sonobe (JP) --

Signed and Sealed this

Eighteenth Day of September, 2007

JON W. DUDAS
*Director of the United States Patent and Trademark Office*

UNITED STATES PATENT AND TRADEMARK OFFICE
CERTIFICATE OF CORRECTION

PATENT NO.      : 7,251,353 B2
APPLICATION NO. : 10/358337
DATED           : July 31, 2007
INVENTOR(S)     : Kunio Doi et al.

It is certified that error appears in the above-identified patent and that said Letters Patent is hereby corrected as shown below:

Column 1, delete lines 16-18, and insert --This invention was made with U.S. Government support grant numbers CA 062625 awarded by the National Institutes of Health (NIH). The U.S. Government has certain rights to the invention--.

Signed and Sealed this

Third Day of June, 2008

JON W. DUDAS
*Director of the United States Patent and Trademark Office*